United States Patent
Sabacinski (10) Patent No.: US 10,695,382 B2
(45) Date of Patent: Jun. 30, 2020

(54) WOUND HEALING COMPOSITIONS AND METHODS OF USE

(71) Applicant: SANMELIX LABORATORIES, INC., Pembroke Pines, FL (US)

(72) Inventor: Kenneth A. Sabacinski, Plantation, FL (US)

(73) Assignee: SANMELIX LABORATORIES, INC., Pembroke Pines, FL (US)

( * ) Notice: Subject to any disclaimer, the term of this patent is extended or adjusted under 35 U.S.C. 154(b) by 0 days.

(21) Appl. No.: 16/664,227

(22) Filed: Oct. 25, 2019

(65) Prior Publication Data

US 2020/0054687 A1 Feb. 20, 2020

Related U.S. Application Data

(63) Continuation of application No. 15/010,896, filed on Jan. 29, 2016.

(60) Provisional application No. 62/109,369, filed on Jan. 29, 2015.

(51) Int. Cl.
| | | |
|---|---|---|
| *A61K 35/644* | (2015.01) | |
| *A61K 31/11* | (2006.01) | |
| *A61L 26/00* | (2006.01) | |
| *A61L 15/46* | (2006.01) | |
| *A61K 9/00* | (2006.01) | |
| *A61K 31/121* | (2006.01) | |
| *A61L 15/40* | (2006.01) | |
| *A61K 33/04* | (2006.01) | |
| *A61K 33/30* | (2006.01) | |
| *A61K 33/00* | (2006.01) | |
| *A61K 33/06* | (2006.01) | |
| *A61L 15/20* | (2006.01) | |

(52) U.S. Cl.
CPC .......... *A61K 35/644* (2013.01); *A61K 9/0014* (2013.01); *A61K 31/11* (2013.01); *A61K 31/121* (2013.01); *A61K 33/00* (2013.01); *A61K 33/04* (2013.01); *A61K 33/06* (2013.01); *A61K 33/30* (2013.01); *A61L 15/20* (2013.01); *A61L 15/40* (2013.01); *A61L 15/46* (2013.01); *A61L 26/0057* (2013.01); *A61L 26/0066* (2013.01); *A61L 2300/102* (2013.01); *A61L 2300/216* (2013.01); *A61L 2300/30* (2013.01); *A61L 2300/404* (2013.01)

(58) Field of Classification Search
CPC .... A61K 9/0014; A61K 31/11; A61K 31/121; A61K 33/00; A61K 33/06; A61K 33/04; A61K 33/30; A61K 35/644; A61L 15/20; A61L 15/46; A61L 26/0057; A61L 26/0066; A61L 2300/102; A61L 2300/216; A61L 2300/30; A61L 2300/404
See application file for complete search history.

(56) References Cited

PUBLICATIONS

Ranzato et al., Honey Exposure Stimulates Wound Repair of Human Dermal Fibroblasts, Jun. 2013, Burns & Trauma, vol. 1 iss. 1, pp. 32-38.*
Fidaleo et al., Methylglyoxal: A New Weapon Against Staphylococcal Wound Infections, Feb. 27, 2010, Chem. Lett., vol. 39, pp. 322-323.*
Majtan et al., Anti-biofilm Effects of Honey Against Wound Pathogens Proteus mirabilis and Enterobacter cloacae, Mar. 11, 2013, Phytotherapy Research, vol. 28, pp. 69-75.*
Berlanga et al., Methylglyoxal administration induces diabetes-like microvascular changes and perturbs the healing process of cutaneous wounds, Clin Sci (Lond), Jul. 2005, vol. 109 iss. 1, pp. 83-95.*

* cited by examiner

*Primary Examiner* — Ali Soroush
(74) *Attorney, Agent, or Firm* — Trueba & Suarez PLLC; Darlene Barron (57) ABSTRACT

The invention provides compositions based on either medicinal honey containing broad spectrum antibacterial activities of peroxide, polyphenols and methylglyoxal, or an effective amount of an active anti-inflammatory ingredient of mineral solids fortified with methylglyoxal antibacterial activity, or a mixture of both for the treatment of wounds; and methods of treating a wound, comprising contacting a wound with any one of the above compositions or a wound dressing containing any one of the above compositions.

14 Claims, 4 Drawing Sheets

WOUND HEALING COMPOSITIONS AND METHODS OF USE

CROSS-REFERENCE TO RELATED APPLICATIONS

This application is a continuation of, and claims priority to, pending U.S. patent application Ser. No. 15/010,896, filed on Jan. 29, 2016, which claims the benefit under 35 U.S.C. § 119(e) of U.S. Provisional Patent Application No. 62/109,369, filed Jan. 29, 2015; which applications are hereby incorporated by reference as if fully set forth herein.

FIELD OF THE INVENTION

The invention broadly relates to wound healing compositions, more specifically to wound healing compositions including various combinations of medicinal honey, methylglyoxal, pharmaceutically acceptable carriers, inorganic minerals with methylglyoxal, salts, and medicinal buckwheat honey.

BACKGROUND OF THE INVENTION

Undesirable and dangerous side effects and adverse drug interactions are well known for the predominantly synthetic organic pharmaceuticals that have been widely administered over the past several decades. These adverse effects have led many research groups to go back and study, in greater detail, the medicinal properties and mechanisms of action of many natural compounds. Ancient cultures have long been aware of the medicinal properties of natural products, such as honey, compounds derived from botanical sources, and compounds from the seas. The subject matter of the present invention involves novel medicinal activities associated with natural products.

In one embodiment of the present invention, various antibacterial mechanisms are combined into a honey. Previously, different antibacterial mechanisms have been known to exist only separately in honeys derived from different floral sources. Honey has been widely accepted as both food and medicine by most, if not all, generations, traditions, and civilizations, both ancient and modern. Although honey has been used by humans for more than 5,000 years to treat a variety of ailments, it has been recognized for almost as long that honeys derived from some floral sources are more medicinal than others. As a general rule, darker honeys have more medicinal activities than light honeys. Many studies have shown that medicinal honey influences biological systems as antioxidant, anti-inflammatory, and antimicrobial. In addition, honey acts as an autolytic debridement agent on wounds, as a cough suppressant, analgesic, remedy for dyspepsia, and natural anti-cancer agent.

One of the darkest honeys is buckwheat honey, which has been shown to have one of the highest antioxidant, anti-inflammatory, and antibacterial activities of any honey variety tested. Because of the bacterial resistance problems that have arisen from the overuse and misuse of antibiotics, the antibacterial activity of honey is the activity that has renewed the interest in honey, particularly for treatment of hard-to-heal (chronic) wounds. But the antibacterial activity of honeys derived from different floral sources has been found to be due to different mechanisms. Early on, honey's antibacterial activity was attributed to its osmotic effect and to its low pH, but these have subsequently been found to contribute only minor antibacterial effects. The first factor discovered that contributes a major antibacterial activity in honey was hydrogen peroxide, but its generation and concentration are under the control of a number of important effects.

First, hydrogen peroxide is not a constituent of the nectar from which honey is produced. It is derived from the enzymatic activity of glucose oxidase acting on glucose. The maturation of honey from plant nectar is dependent upon the activities of several enzymes, most of which are derived from the hypopharyngeal gland of the honey bee. Diastase (amylase), derived from the bee, breaks down starch to smaller carbohydrates (dextrins, oligo-, di- and monosaccharides [glucose]). Invertase, derived from the bee, converts sucrose, the primary sugar in nectar, into glucose and fructose. Glucose oxidase, also derived from the bee, catalyzes the oxidation of glucose by molecular oxygen to gluconolactone, which subsequently hydrolyses spontaneously to gluconic acid and hydrogen peroxide. Gluconic acid is the primary acid in honey responsible for most of honey's acidity and low pH, and hydrogen peroxide is the primary antibacterial agent in most medicinal honeys.

Second, the production of hydrogen peroxide is very slow in mature honey for two reasons: i) the activity of glucose oxidase is depressed by high osmotic pressure, and ii) the spontaneous conversion of gluconolactone to glucuronic acid and hydrogen peroxide is a hydrolysis reaction requiring water, which is unavailable in ripe honey. Most hydrogen peroxide present in ripe honey is generated as the honey is being ripened and dried by the bees. And when ripened honey is subsequently diluted, by wound fluid for example, this reaction speeds up again. Upon dilution of medicinal honey, the rate of hydrogen peroxide generation is continuous and can reach concentrations up to 4 mmol/L, with a mean of about 1-2 mmol/L. This relatively low concentration is nevertheless high enough to provide a substantial antibacterial activity, and yet is about 1000-times less than the 3% solution commonly used as an antiseptic; which has been associated with tissue damage, including damage to fibroblast cells from human skin. Furthermore, the continuous production of hydrogen peroxide in diluted honey produces a long-lasting antiseptic effect that is most sought after in fighting infections in wounds. It has been reported that hydrogen peroxide is more effective when supplied by continuous generation from glucose oxidase catalysis, as in honey, than when added as a single bolus.

Third, in addition to the glucose/glucose oxidase system as a main source of hydrogen peroxide generation, plant-derived polyphenols present in some honeys provide a supplementary source of hydrogen peroxide. Honeys with high concentrations of polyphenols, such as buckwheat honey, have higher hydrogen peroxide levels due to this second method of hydrogen peroxide generation. The mechanism of this action is likely from the auto-oxidation of polyphenols yielding both hydrogen peroxide and phenoxyl-radicals. Furthermore, redox-active phenolics appear to be active intermediates that confer additional oxidative activity on hydrogen peroxide. In addition, the chemical interaction of honey phenolics with hydrogen peroxide results in products that degrade bacterial DNA. In the presence of transition metal ions, via the Fenton reaction, hydrogen peroxide is also converted to hydroxyl radicals. Both the phenoxyl- and hydroxyl-radicals have been shown to induce strand breaks in DNA. Thus, a second factor present in some honeys that contribute to its antibacterial effect are polyphenols.

A third factor found in honey that has antibacterial activity is methylglyoxal (MGO), but this agent has only been found in honey derived from certain floral species of the *Leptospermum* genus of shrubs and small trees found in New Zealand, Australia, Malaysia, and Indonesia. Originally referred to as UMF (Unique Manuka Factor), methylglyoxal has been found to originate in honey from dihydroxyacetone present in the nectar of *Leptospermum* flowers, for example from the manuka tea tree (*Leptospermum scoparium*) of New Zealand or the jelly bush (*Leptospermum polygalifolium*) of Australia. Since the first description of UMF, it has been recognized that its concentration is highly variable in different manuka honey batches, and that has been determined to be due to different concentrations of dihydroxyacetone in different cultivars of manuka, with pink-flowered cultivars producing the highest dihydroxyacetone levels in nectar. There are also seasonal changes within a *Leptospermum* species, or between the different species. Because of this batch-to-batch variability, the methylglyoxal levels or antibacterial activity of each lot of *Leptospermum* honey must be assayed to determine whether it will be useful as a medicinal honey or not. As manuka honey often has very low levels of hydrogen peroxide, methylglyoxal becomes its primary antibacterial agent.

A fourth antibacterial factor that has been found in Revamil Source honey that is produced in greenhouses in The Netherlands is Bee Defensin-1, a cationic antimicrobial peptide placed in this honey variety by the bees. Defensins are antimicrobial peptides found in many organisms, including plants, invertebrates, insects, birds and mammals. They are cysteine-rich peptides with multiple disulfide bonds and a triple-stranded beta sheet. Most defensins function by binding to the microbial cell membrane, and once embedded, they form pore-like membrane defects that allow efflux of essential ions and nutrients. Bee Defensin-1, a 51-amino acid peptide (also called Royalisin because it was first discovered in royal jelly), was discovered in Revamil Source honey when bactericidal activity was not eliminated by neutralization of the usual antimicrobial factors (hydrogen peroxide and methylglyoxal). The activity was found in a relatively high molecular weight (>5-kDa) chromatographic fraction; stained as a protein on polyacrylamide gel electrophoresis, and was immuno-stained by anti-bee defensin-1 antibody on a Western blot. In addition, the antibacterial activity of Revamil Source honey was abolished by proteolytic digestion with pepsin and by the anti-bee defensin-1 antibody.

Medicinal honeys from different floral sources exhibit differing antibacterial activities towards different bacterial pathogens. For example, Mundo et al., (2004) reported varying sensitivities to the antibacterial properties of 26 different honey types by nine different bacteria, including multiple strains of *Staphylococcus aureus*, emphasizing the variability in the antibacterial effect of different honey samples. These authors reported that whereas *Bacillus stearothermophilus* was the most sensitive microorganism to the antibacterial activity of medicinal honeys in this study, *Alcaligenes faecalis*, *Lactobacillus acidophilus*, and *Staphylococcus aureus* strains ATCC 25923, 8095, and 9144 were each moderately sensitive, and *Escherichia coli*, *Salmonella enterica*, *Pseudomonas fluorescens*, *Bacillus cereus*, and *Listeria monocytogenes* were the most resistant to the antibacterial activity of honey.

In this study it was demonstrated that different microorganisms were more or less susceptible to the different antibacterial mechanisms in various honeys. Whereas it required 50% manuka honey with its non-peroxide methylglyoxal antibacterial mechanism to inhibit the growth of *B. stearothermophilus*, buckwheat honey at only 25% concentration was required to inhibit the growth of this organism via its hydrogen peroxide-dependent antibacterial action. The same was true for the inhibition of *S. aureus* strains ATCC 9144 and 25923 which both were inhibited by 50% manuka honey but by only 33% buckwheat honey, whereas the converse was true for the inhibition of *S. aureus* strain ATCC 8095 and *B. cereus* where 50% buckwheat honey was required to completely inhibit their growth while only 25% manuka honey was required. Table 1 summarizes the bacterial sensitivities of the various bacteria to the different honeys.

TABLE 1

Bacterial Sensitivity by Type and Inhibitory Concentration of Honey.

| Bacteria | Type of Honey and (Inhibitory Concentration; Bacteria % honey in water, w/v) |
|---|---|
| *E. coli* O157:H7 | christmas berry (100); saw palmetto (100); tarweed (100); buckwheat (100); manuka (50) |
| *S. enterica* | manuka (50) |
| *A. faecalis* | blueberry (100); soybean (100); tarweed (33); buckwheat (33); manuka (25); horsemint (25) |
| *P. fluorescens* | tarweed (100); buckwheat (50) |
| *L. acidophilus* | soybean (100); christmas berry (100); buckwheat (100); manuka (100); saw palmetto (100); melaleuca (50); tarweed (50) |
| *L. monocytogenes* | melaleuca (100); tarweed (100); buckwheat (100) |
| *B. cereus* | tarweed (100); buckwheat (50); manuka (25) |
| *S. aureus* ATCC 8095 | christmas berry (100); saw palmetto (50); tarweed (50); buckwheat (50); cotton (33); manuka (25) |
| *S. aureus* ATCC 9144 | saw palmetto (100); sunflower (100); horsemint (100); manuka (50); melaleuca (33); buckwheat (33) |
| *S. aureus* ATCC 25923 | soybean (100); sunflower (100); saw palmetto (50); melaleuca (50); rabbit bush (50); manuka (50); tarweed (33); buckwheat (33) |
| *B. Stearothermophilus* | blueberry (100); blackberry (100); manuka (50); black sage (50); red sumac (50); melaleuca (50); horsemint (50); christmas berry (50); soybean (33); alfalfa (33); cotton (33); saw palmetto (33); rabbit bush (33); tarweed (25); buckwheat (25); knotweed (20); sunflower (17) |

Data from Mundo et al., 2004.

Of the honeys listed in Table 1, buckwheat, tarweed, saw palmetto and melaleuca inhibit bacteria primarily via hydrogen peroxide, whereas the antibacterial activity of manuka, blueberry, and knotweed honeys is primarily non-peroxide mediated. Other studies report similar findings and therefore the present disclosure relates to a honey composition containing high concentrations of both peroxide and non-peroxide antibacterial activities in order to produce a honey with broad-spectrum antibacterial activity efficient at inhibiting growth of most major wound pathogenic bacteria at one low honey concentration.

Plants have also been used for medicinal purposes since before recorded history. Ancient Chinese and Egyptian papyrus writings describe medicinal uses for plants as early as 3,000 BC. While some cultures, such as Africans and Native Americans, have used botanical sources in their healing remedies, other cultures including the Chinese and Indians have developed medicinal systems, such as Traditional Chinese Medicine and Ayurveda, respectively, in which botanicals were used. Modern researchers have found that people in different parts of the world used the same or similar plants for the same purposes.

In the early 19th Century, when chemical analysis first became available, scientists began to extract and modify the active ingredients from botanical sources. Today almost one quarter of pharmaceutical drugs are derived from botanicals. Recently, the World Health Organization (WHO) estimated that 80% of people worldwide rely on botanical medicines for some part of their primary health care. Botanical medicine is being taught more in medical schools and pharmacy schools, and more health care providers are learning about the positive effects of using botanical medicine to help treat health conditions. In Germany, for example, about 600-700 plant-based medicines are available and are prescribed by some 70% of German physicians. In the past 20 years in the United States, public dissatisfaction with the cost of prescription medications and their extensive adverse effects, combined with an interest in returning to more natural remedies, has led to an increase in botanical medicine use. Botanical medicine is used to treat many conditions, such as asthma, eczema, premenstrual syndrome, menopausal symptoms, rheumatoid arthritis, migraine, chronic fatigue, irritable bowel syndrome, cancer and chronic wounds among others. Today, nearly one-third of Americans use herbs and one study found that 90% of arthritic patients use alternative therapies such as botanical medicine.

One such botanical remedy originated in American Indian folklore as a treatment for hard-to-heal wounds. It was handed down to the pioneers in South Carolina as an extract of ash derived specifically from Red Oak Bark grown in the region around Piedmont, S.C. A paste of this extract that was applied to a hard-to-heal wound or skin ulcer proved to be very effective at healing the wound. It is now known that Red Oak Bark contains specific storage cells that collect and concentrate certain mineral ions from the soil in which they grow, and that the soil around Piedmont, S.C. contained a high level of specific minerals that are key for healing wounds. Chemical analyses of the extracts from the ash of Red Oak Bark led to the identification of the minerals responsible for the wound healing effect and a safe and efficacious version of the active minerals, which included potassium, calcium, zinc and rubidium is now manufactured by combining these minerals in a proprietary formulation and used for chronic wound therapy. U.S. Pat. No. 5,080,900 described the oak bark ash extract and U.S. Pat. Nos. 6,149,947 and 7,014,870 described the synthetic version of the formulation. All three patents are now expired.

In one study, Weindorf et al., (2012) demonstrated that the synthetic formulation of these ions prepared in the pharmaceutically-accepted carrier of polyethylene glycols used to treat over 300 therapy-refractory wounds, demonstrated a wound size reduction of at least 50% in 73% of the patients, where a wound size reduction of at least 50% is predictive of successful wound closure.

As with plants, the marine ecosystem has been a source of therapeutics for the treatment of human diseases. In recent times, cancer drugs have been developed from marine sources. Cytosar, a staple treatment for leukemia and lymphoma was derived from a Caribbean sea sponge. Other anti-cancer drugs have been derived from tunicates and a potent medicine for the treatment of chronic pain, more powerful than morphine, has been derived from the venom of cone snails that inhabit the reefs of Australia, Indonesia and the Philippines. The waters of the Dead Sea have been renowned for their therapeutic effects since ancient times. Galenus, a prominent first Century Greek physician, stated that this salt water was good for the treatment of arthritis, eczema, muscular pain, rheumatism, and psoriasis, and the Jewish-Roman historian, Flavius Josephus, wrote two thousand years ago that the salts from the Dead Sea heal the human body and are therefore used in many medicines.

The water of the Dead Sea is unique compared to other seas and lakes in its high concentration of salts--Dead Sea water contains 330 g of minerals per liter (33%). This salt concentration is between 7-10 times that of the oceans, which typically contain 3.5% minerals. The mineral composition of the Dead Sea is also significantly different from that of ocean water. Whereas the major salt constituent of ordinary seawater is sodium chloride (NaCl), Dead Sea salt is rich in $MgCl_2$, $CaCl_2$, KCl, $MgBr_2$ and $CaSO_4$. The concentration of ionic species present in the Dead Sea water is: magnesium (40.65 g/L), sodium (39.15 g/L), calcium (16.86 g/L), potassium (7.26 g/L), chloride (212.4 g/L), bromide (5.12 g/L), sulfate (0.47 g/L), and bicarbonate (0.22 g/L). The bromide ion concentration is the highest of all waters on the earth and serum bromide levels have been shown to increase up to 4-fold after bathing in the Dead Sea for four weeks, as a result of entering the circulation and internal organs through the skin. Metal ions are required for many critical functions in humans. Scarcity of some metal ions often leads to disease. Four main group metals (Na, K, Mg, and Ca) and 10 transition metals (V, Cr, Mn, Fe, Co, Ni, Cu, Zn, Mo, and Cd) are currently known or thought to be required for normal biological function. It is believed that the therapeutic properties of the Dead Sea are due to a large extent to the presence of magnesium, potassium and bromide.

Various cultures and groups of people have visited the Dead Sea for therapy, dating back to the time of the ancient Egyptians, utilizing the salt in various unguents and skin creams, as well as soaps, just as it is used today. The Dead Sea has taken on a new dimension today: modern science has proven the therapeutic and rejuvenating properties of its unique mineral content. The Dead Sea has become a renowned center for natural health with people coming from around the world to bath in its mineral-rich waters. Balneotherapy emerged as an important treatment modality in the 1800s, first in Europe and then in the United States. After seeing decline in use for almost 50 years, at about the same time as the decline in the use of medicinal honey, balneotherapy in the Dead Sea has experienced resurgence in popularity over the past two decades at the same time as a new recognition of the safety and efficacy of natural remedies has fueled a resurgence in popularity for these treatment modalities. The major dermatological diseases that are frequently treated by baloneotherapy in the Dead Sea with a high rate of success are psoriasis and atopic dermatitis. Both magnesium and potassium ions from the Dead Sea have a specific inhibitory capacity on the uncontrolled proliferation of psoriatic dermis grown in tissue culture.

Magnesium salts, the prevalent minerals in Dead Sea salt, are known to exhibit favorable effects in inflammatory diseases. In one study of atopic dry skin, bathing in magnesium-rich Dead Sea salt solution improved skin barrier function, enhanced skin hydration, and reduced inflammation. In other in vitro and in vivo studies, magnesium ions inhibit the number and function of epidermal Langerhans cells that contribute to inflammatory skin diseases by presenting alloantigens to T lymphocytes, thereby activating these cells to release pro-inflammatory cytokines. In one study, the reduced antigen presenting activity of $MgCl_2$-treated Langerhan's cells was associated with suppression of constitutive tumor necrosis factor (TNF)-$\alpha$ production by the epidermal cells in vitro. Another study showed that Dead Sea water inhibited the production and/or release of the pro-inflammatory cytokines, interleukin (IL)-2 and interferon (IFN)-.gamma., from Th1 lymphocytes. Others confirmed down-regulation of the pro-inflammatory cytokines, TNF-.alpha. and IL-1, and an up-regulation of insulin-like growth factor (IGF)-1 following balneotherapy in the Dead Sea.

Magnesium impacts more than 325 enzyme systems in the human body. For example, it is a rate-limiting factor in the activation of epidermal adenylate cyclase and consequently in the production of cyclic adenosine monophosphate (cAMP). A decrease of cAMP and concomitant increase of cyclic guanosine monophosphate (cGMP) has been implicated in excessive cellular proliferation, a major element of the psoriatic state. Balneotherapy in Dead Sea water has also been applied to the treatment of various inflammatory rheumatic diseases such as rheumatoid arthritis and psoriatic arthritis. In a study of Dead Sea water in the treatment of patients with rheumatoid arthritis, Dead Sea water produced statistically significant clinical improvements in most parameters for up to one month following cessation of treatment, whereas treatment with sodium chloride water did not. Dead Sea balneotherapy for 14 days also produced significant clinical improvements in knee osteoarthritis, which lasted for at least 1 month following cessation of treatment. Many other diseases are also treated by balneotherapy in the Dead Sea, including chronic ulcers.

Hypertonic Dead Sea water has also been shown to be efficacious in the treatment of allergic rhinitis. The two common treatments for such sinonasal disease are intranasal rinsing with normal saline solution or corticosteroid rinses, and both have positive effects on the physiology of nasal mucosa. In a study comparing Dead Sea saline spray with NaCl solution, the hypertonic Dead Sea saline solution proved efficacious in mild-to-moderate allergic rhinitis, including improving mucociliary clearance, whereas no significant improvement was seen with the nasal saline spray.

DePootere et al., (2011) demonstrated that the addition of magnesium and bromide to some of the botanically-derived inorganic metal ions gave an enhanced anti-inflammatory and wound healing effect in an animal model of chronic rhinosinusitis. The present invention adds antibacterial and anti-biofilm activities to the anti-inflammatory activity of the mineral salts composed of a mixture of active ingredients from two sources: a tree bark, and the Dead Sea.

As can be derived from the variety of devices and methods directed at wound healing compositions, many strategies have been contemplated to accomplish the desired end. Heretofore, widely administered synthetic organic pharmaceuticals are commonly associated with undesirable side effects and adverse drug interactions. Thus, there is a long-felt need for more natural wound healing compositions. There is a further long-felt need for wound healing compositions involving medicinal honey, mineral ions, and methylglyoxal, and their corresponding methods of use.

BRIEF SUMMARY OF THE INVENTION

The first inventive composition of the present disclosure is a medicinal honey with concentrations of hydrogen peroxide, polyphenols and methylglyoxal that are all in the upper concentration range of what are naturally found in various native honeys. This is achieved by fortification of buckwheat honey that is naturally rich in hydrogen peroxide and polyphenols with methylglyoxal. In this first composition of the present invention, 'MGO-fortified buckwheat honey' provides a composition containing buckwheat honey with high natural concentrations of hydrogen peroxide and polyphenols to which methylglyoxal is added to a concentration between 500-2000 mg per kg of final honey product. The phrase 'high natural concentrations of hydrogen peroxide and polyphenols' is defined as concentrations that naturally exist in buckwheat honey where the concentration of hydrogen peroxide is in the range of 2-4 mM and where the polyphenol concentration is in the range of 275-575 gallic acid equivalents per gram of honey.

A second composition of the present invention includes a mixture of ingredients originally isolated from a botanical source, with ingredients originally isolated from the Dead Sea, to yield an active source of anti-inflammatory activity that down-regulates protease gene expression in chronic wounds. To this embodiment of this inventive composition of a mixture of botanical- and oceanic-derived inorganic minerals, methylglyoxal is added to supplement its anti-inflammatory activity with non-peroxide antibacterial activity. This composition, herein referred to as "MVE ointment with MGO," (wherein 'MVE' denotes 'multivalent electrolytes') includes an active anti-inflammatory ingredient of inorganic mineral solids including salts of magnesium, potassium, calcium, zinc, rubidium, bromide, and sulfate to which is added non-peroxide antibacterial activity in the form of the natural compound, methylglyoxal.

A third composition of the present invention includes a mixture of 'MGO-fortified buckwheat honey' (composition 1) and 'MVE ointment with MGO' (composition 2); the mixture may be made using different ratios of composition 1 and composition 2 (ranging between 1:9 and 9:1 [v/v]) and gives rise to composition 3, herein referred to as 'buckwheat honey with MVE and MGO.' In this composition, the active anti-inflammatory ingredient of inorganic mineral solids including salts of magnesium, potassium, calcium, zinc, rubidium, bromide, and sulfate is supplemented with the antibacterial activity of medicinal buckwheat honey fortified with methylglyoxal, which has broad-spectrum antibacterial activity because it includes both peroxide and non-peroxide antibacterial compounds (hydrogen peroxide, polyphenols and methylglyoxal). This third inventive composition includes a mixture of antibacterial medicinal buckwheat honey naturally rich in hydrogen peroxide and polyphenols, a non-peroxide antimicrobial compound, methylglyoxal, naturally found both in mammalian tissues and in *Leptospermum* honeys, and an anti-inflammatory active ingredient of inorganic solids including salts of magnesium, potassium, calcium, zinc, rubidium, bromide, and sulfate.

All three of the inventive compositions are used in aqueous, ointment, or wound-dressing formulations to modulate biochemical mechanisms associated with wound healing, including decreasing both wound protease activities and active infection.

These and other objects and advantages of the present invention will be readily appreciable from the following description of preferred embodiments of the invention and from the accompanying examples and claims.

BRIEF DESCRIPTION OF THE DRAWINGS

The nature and mode of operation of the present invention will now be more fully described in the following detailed description of the invention taken with the accompanying figures, in which.

DETAILED DESCRIPTION OF THE INVENTION

While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

The present invention provides three exemplary wound healing compositions. The first composition includes seasonally harvested raw, strained, monofloral buckwheat honey naturally rich in hydrogen peroxide (containing and/or capable of generating 2-4 mM concentration), polyphenols (275-575 gallic acid equivalents of polyphenol compounds per gram of honey) to which is added the natural antibacterial compound, methylglyoxal to a final concentration of 500-2000 mg per kg of final honey product. This MGO-fortified buckwheat honey has broad-spectrum antimicrobial activity effective to reduce the number of viable microorganisms at a wound site.

A second composition of the present invention includes a pharmaceutically-acceptable carrier, an effective amount of an active mixture of inorganic minerals, and an amount of methylglyoxal (500-2000 mg per kg of final composition two product) that effectively reduces the number of viable microorganisms at a wound site. The active mixture of inorganic minerals include, but are not limited to, a magnesium salt, a potassium salt, a calcium salt, a zinc salt, and a rubidium salt, wherein each of the salts include a pharmaceutically-acceptable anion including bromide, chloride, citrate, and sulfate.

A third composition of the present invention comprises a mixture of compositions 1 and 2 including a pharmaceutically-acceptable carrier, an effective amount of an active mixture of inorganic minerals, medicinal buckwheat honey that contains, or is capable of generating 2-4 mM hydrogen peroxide, and 275-575 gallic acid equivalents of polyphenol compounds per gram of honey, and methylglyoxal to a final concentration of 500-2000 mg per kg of composition 3 (buckwheat honey with MVE & MGO) such that the composition is endowed with broad spectrum antibacterial activity effective to reduce the number of viable microorganisms at a wound site. The active mixture of inorganic minerals includes, but is not limited to, a magnesium salt, a potassium salt, a calcium salt, a zinc salt, and a rubidium salt, wherein each of the salts includes a pharmaceutically-acceptable anion including bromide, chloride, citrate, and sulfate.

In any embodiment of the second and third compositions, the active mixture of inorganic minerals includes at least one of 1.5-75 parts of magnesium ions, 0.5-75 parts of potassium ions, 0.001-10 parts of calcium ions, 0.0001-10 parts of zinc ions, up to 5 parts of rubidium ions, 10-80 parts of chloride ions, 0-40 parts of citrate ions, 0.001-20 parts of bromide ions, and up to 20 parts of sulfate ions, said parts being expressed as parts by weight of the total inorganic mineral solids. In any of the above embodiments, methylglyoxal is added to a concentration in the final formulation of between 500-2000 mg/kg. To make composition three, a volume of the complete composition two formulation of mineral salts plus methylglyoxal in a pharmaceutically-acceptable carrier is mixed with 10-90 parts of MGO-fortified buckwheat honey (composition one), per 100 parts total, said parts being expressed as parts by volume of the final formulation, where the medicinal honey also contains methylglyoxal at a concentration between 500-2000 mg per kg of honey.

Composition two includes a pharmaceutically-acceptable carrier, such as but not limited to a carrier including at least one of water, polyethylene glycol, an ointment, and a cream base, which results in a therapeutic composition having a pH in the range of 3-7.5, inclusive. Preferably, the composition has a pH in the range of 3.5-6.5, inclusive. As used herein, a composition comprising "MVE salts" refers to a composition that includes magnesium, potassium, calcium, zinc, and rubidium cations, together with pharmaceutically acceptable counterions including bromide and sulfate anions.

In another aspect, the present invention provides a wound dressing. The wound dressing is used with any of the above embodiments of the composition and a support. In any embodiment of the dressing, the support includes, but is not limited to, a fibrous gauze material, a hydrogel, a foam, a film, a hydrocolloid, an alginate, a collagen, or a combination of any two or more of the afore-mentioned.

In yet another embodiment, the present invention includes a method of treating a wound. The method includes contacting a wound with any of the above embodiments of the wound dressing.

A "chronic wound", "non-healing wound," slow-to-heal wound," or "stalled wound," as used herein, refers to a wound that fails to heal over a 4-12 week timeframe from inception of the wound to complete closure of the skin at the wound site. Such wounds commonly include external dermal wounds or wounds of mucosal membranes such as sinonasal or endometrial wounds.

Skin wounds designated as "chronic" or "non-healing" or "slow-to-heal" or "stalled" are commonly observed in clinical settings as venous leg ulcers, diabetic foot ulcers, pressure ulcers, arterial ulcers, ulcers of mixed etiology, burns, or non-healing surgical wounds. Other types of non-healing wounds are observed in less frequent conditions, such as, fistulae, dermatitis or vasculitis wounds, skin cancers, and radiation burns. This list is not exhaustive and is provided to show examples of such non-healing wounds. Differentiated from "acute" wounds that spontaneously heal without complications in a matter of days or weeks through the four normal phases of the "wound-healing curve" (hemostasis, inflammation, proliferation, and remodeling), chronic wounds may persist for months or years and occasionally can last a lifetime, and are therefore commonly referred to as "non-healing" wounds. There is a need for treatment of any of these types of non-healing wounds since spontaneous healing has failed to occur. In chronic wounds, at the cellular biological level, there is commonly a prolonged inflammatory phase often caused by elevated proteases or active infection.

In yet another embodiment of the present invention, the various compositions are used prophylactically to prevent surgical wounds in high-risk patients from post-operative wound dehiscence and non-healing. More than 53 million people undergo surgical procedures annually in the United States, with about half of these occurring under general anesthesia. Post-operative wound dehiscence has been investigated in several studies and a small incidence has shown to be an issue of concern in all age groups, including the pediatric population, but with a higher incidence in the older population. The failure of these surgical wounds to heal in a normal time frame pushes them into the category of chronic wounds. Diabetes, obesity, cancer therapy, and vascular abnormalities, which are all increasing in incidence in the Western population, contribute to delayed healing and are considered risk factors. The prophylactic application of any of the present inventive compositions to surgical incisions post-operatively in 'high-risk' patients will aid in reducing the incidence of non-healing surgical wounds.

Some prolonged inflammation and active infections occur simultaneously and prevent wounds of the skin or mucosal membranes from healing. The present disclosure relates to compositions, carriers, and methods for treating wounds of the skin and mucosal membranes. The compositions include medicinal honey fortified with the additional antimicrobial methylglyoxal compound, and an active ingredient of a mixture of inorganic solids originally derived from botanical and Dead Sea sources and including magnesium, potassium, calcium, zinc, rubidium, bromide, and sulfate. The components of the inventive composition surprisingly provide a synergistic effect that results in the suppression of the accumulation of a biochemical marker (e.g. proteases, and pro-inflammatory cytokines) associated with inflammation, and the up-regulation of other biochemical markers (e.g. growth factors and protease inhibitors) associated with wound healing. In addition, the components of the inventive compositions provide antibacterial activity that acts concomitantly with the anti-inflammatory activity to also provide suppression of active infections.

Compositions according to the present invention are useful for treating common chronic wounds, such as venous leg ulcers, diabetic foot ulcers, pressure ulcers, arterial ulcers, burns, non-healing surgical wounds, chronic rhinosinusitis and metritis. In addition, compositions according to the present invention are also useful for treating abrasions, lacerations, minor cuts, scalds and burns, and other partial thickness wounds. Useful compositions include, but are not limited to, medicinal honey, methylglyoxal, magnesium, potassium, calcium, zinc, rubidium, bromide and sulfate. The compositions are advantageously applied in a cream or ointment base that is applied to a wound until it is healed (3-8 months) with wound dressing changes every 24-96 hours. Alternatively, the wound healing compositions of the present invention are impregnated into or associated with carrier dressing supports (e.g. fibrous gauze, hydrogel, foam, film, hydrocolloid, collagen, or alginate), which are applied to wounds for the times described above.

The present disclosure further provides a method for treating the wound. In some embodiments, the method includes contacting a wound with any composition of the present disclosures wherein the composition includes a medicinal honey fortified with the natural non-peroxide antibacterial compound, methylglyoxal; a pharmaceutically-acceptable carrier; an effective amount of an active ingredient of inorganic solids comprising a magnesium salt, a potassium salt, a calcium salt, a zinc salt, a rubidium salt, a bromide salt, and a sulfate salt; and the natural non-peroxide antibacterial compound, methylglyoxal comprising of an amount between 500-2000 mg per kg of finished wound healing compositions, effective to reduce the number of viable microorganisms at a wound site. The compositions are applied to the wound, for example, in a liquid, (e.g. by irrigating or lavaging the wound with the liquid) or in a gel or an ointment. Liquid compositions provide immediate availability of the ions and methylglyoxal to the healing tissue. In contrast, gels or ointments can provide regulated delivery of the ions, medicinal honey, and methylglyoxal to the healing tissue over a sustained period of time. In some embodiments, the composition is applied to a wound dressing, which is subsequently applied to the wound. Advantageously, a dressing including any of the compositions is contacted with the wound until it is healed (3-8 months) with wound dressing changes every 24-96 hours, thereby providing a moist environment enriched with the MGO-fortified medicinal honey, or the MVE ions and methylglyoxal, or a mixture of both to facilitate healing of the skin or mucosal membrane.

EMBODIMENTS

Embodiment 1 is a composition including a medicinal honey with high peroxide-induced and polyphenol-facilitated antimicrobial activity, an effective amount of methylglyoxal (500-2000 mg/kg) to add non-peroxide antimicrobial activity, wherein each of the antimicrobial activities provides a different mechanism of antibacterial inhibition thereby providing a broad spectrum antimicrobial activity effective to reduce the number of viable microorganisms at a wound site.

Embodiment 2 is the composition of embodiment 1 wherein the medicinal honey is monofloral buckwheat honey that naturally generates 2-4 mM hydrogen peroxide and which naturally contains 275-575 gallic acid equivalents of polyphenol compounds per gram of honey, and wherein the amount of methylglyoxal added is 500-2000 mg per kg of honey.

Embodiment 3 is a composition including a pharmaceutically-acceptable carrier, an effective amount of an active ingredient of inorganic solids including a magnesium salt, a potassium salt, a calcium salt, a zinc salt, a rubidium salt, a bromide salt, and a sulfate salt; and methylglyoxal as an antimicrobial at an amount between 500-2000 mg/kg, which is effective to reduce the number of viable microorganisms at a wound site, wherein each of the salts includes a pharmaceutically acceptable counterion.

Embodiment 4 is the composition of embodiment 3, wherein the active ingredient of inorganic solids includes 1.5-75 parts of magnesium ions, 0.5-75 parts of potassium ions, 0.001-10 parts of calcium ions, 0.0001-10 parts of zinc ions, up to 5 parts of rubidium ions, 0.001-20 parts of bromide ions, and up to 20 parts of sulfate ions (said parts being expressed as parts by weight of the total weight of inorganic solids), and methylglyoxal representing 500-2000 mg/kg of the final composition.

Embodiment 5 is a mixture of embodiment 2 and embodiment 4, wherein the ratio of embodiment 2 to embodiment 4 is between 1:9 and 9:1 by volume.

Embodiment 6 is a wound dressing including the composition of any of embodiments 1 through 5; and a support.

Embodiment 7 is the wound dressing of embodiment 6, wherein the support includes a fibrous gauze material, a hydrogel, a foam, a film, a hydrocolloid, an alginate, a collagen, or a combination of any two or more of the afore-mentioned.

Embodiment 8 is a method of treating a wound, including contacting a wound with the composition of any one of embodiments 1 through 5.

Embodiment 9 is a method of treating a wound, including treating a wound with the wound dressing of either one of embodiments 6 or 7.

EXAMPLES

Objects and advantages of this invention are further illustrated by the following examples, but the particular materials and amounts thereof recited in these examples, as well as other conditions and details, should not be construed to unduly limit this invention.

Example 1 Demonstrates Composition 1, Embodiments 1 and 2

Monofloral buckwheat honey fortified with methylglyoxal at a concentration of 1000 mg/kg is prepared and impregnated into acetate non-woven medical grade dressing (approximately 4 g MGO-fortified buckwheat honey in each 4".times.5" dressing). The dressings are protected with polyethylene liners applied to both sides, and dressings of 4".times.5" are sealed individually in foil pouches constructed of white polyester film fused to aluminum foil that constitutes an excellent barrier. The dressings are then sterilized with gamma radiation and verified as sterile before use.

Figure 1:
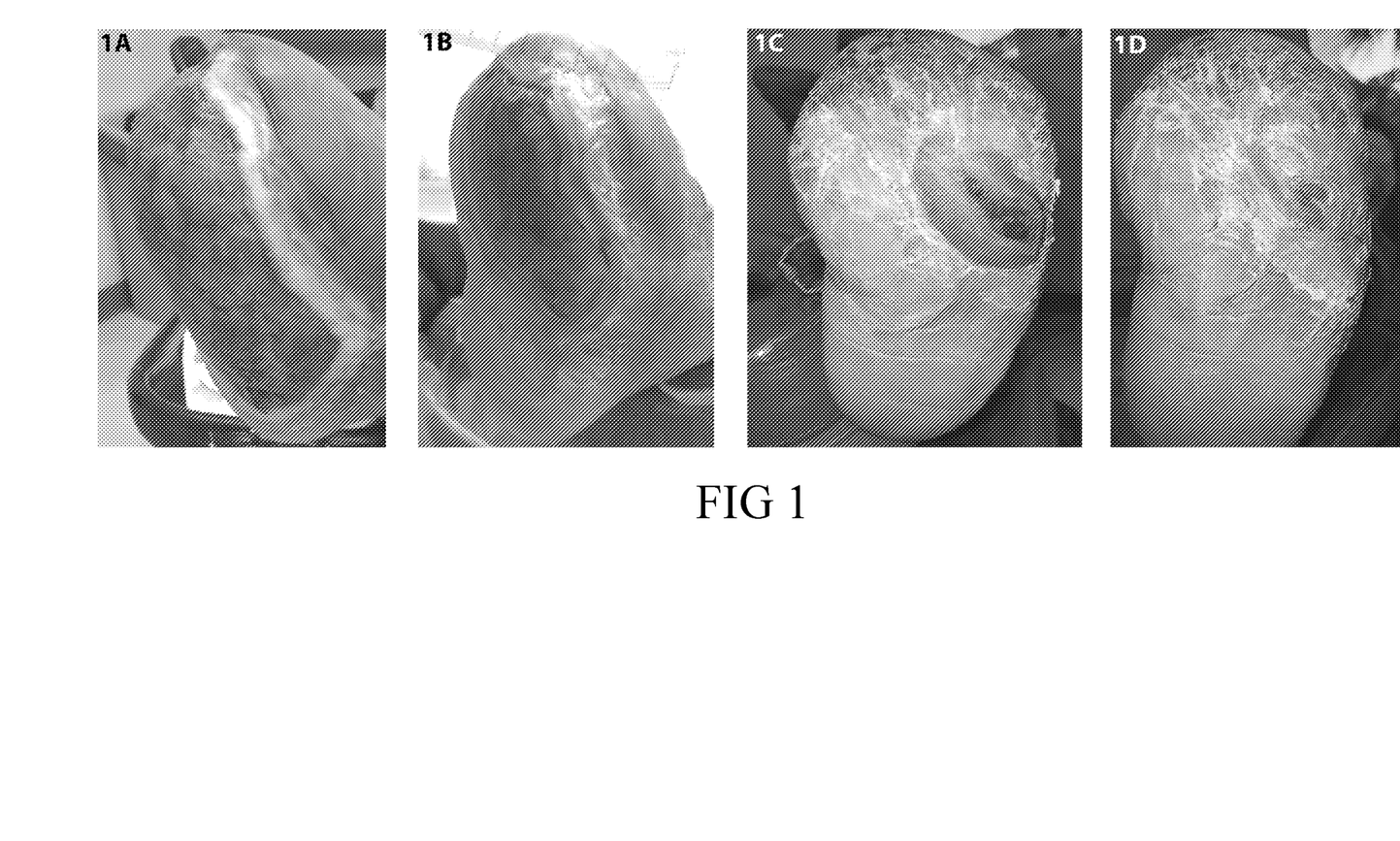
FIG. 1, panels 1A, 1B, 1C, and 1D, shows treatment using composition 1 of the present invention, MGO-fortified buckwheat honey wound dressings of a large infected amputation wound in the foot of a diabetic patient.

Panels 1A, 1B, 1C, and 1D of FIG. 1, show treatment using dressings impregnated with composition 1 of the present invention, MGO-fortified buckwheat honey, of a large infected open amputation wound in the foot of a diabetic patient. A 47 year-old male with a history of plantar diabetic foot ulcers who had recently had all the toes on his left foot amputated and the dermal layer on a significant portion of the underside of his foot excised to remove infected tissue (Panel 1A) presented with extensive infection in the open wound on the plantar aspect of his foot. After sharp debridement of this severely infected open amputation wound to remove slough, eschar, and necrotic tissue, the manufactured MGO-fortified buckwheat honey dressings were cut to closely fit the wound using sterile scissors and applied to the wound, with dressing changes every two days. On day 0, the wound measured 12 cm.times.8 cm (Panel 1A: wound area 96 cm.sup.2). The patient was instructed on how to change his own dressings every 48 hours. After three weeks of treatment with the sterile MGO-fortified buckwheat honey dressings, the wound area decreased 7.8-fold to 12.25 cm.sup.2 (Panel 1B), a wound area reduction of 87%. Many wound healing trajectory studies in the literature indicate that a wound area reduction of greater than 50% within 4 weeks of treatment indicates that full wound closure will occur within 12-20 weeks of continued treatment. This wound was no exception to that expectation, fully closing after 12 weeks of treatment with the MGO-fortified buckwheat honey dressings, having a wound area of 2.6 cm.sup.2 after 8 weeks of treatment (Panel 1C), and less than 0.4 cm.sup.2 after 11 weeks of treatment (Panel 1D).

Example 2 Demonstrates Composition 1, Embodiments 1 and 2

Figure 2:
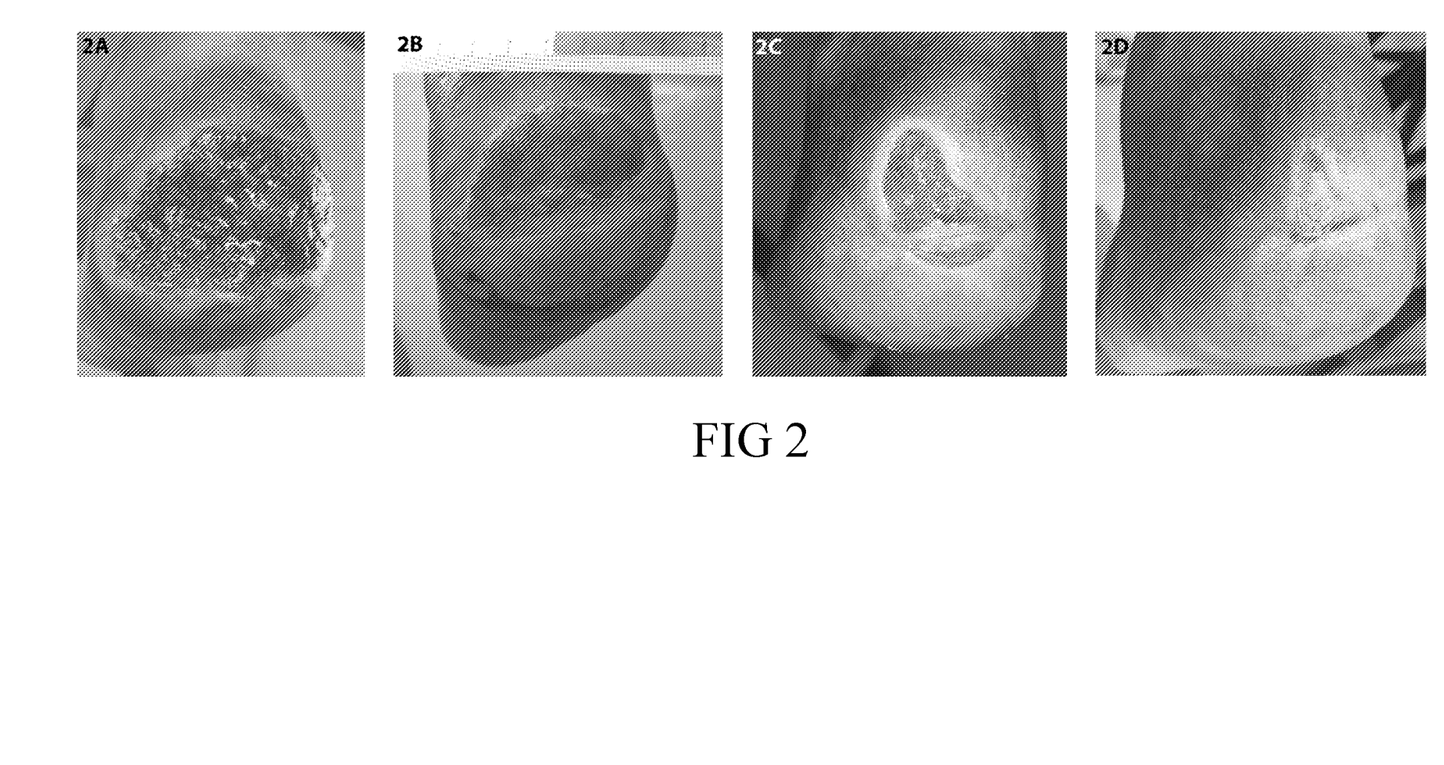
FIG. 2, panels 2A, 2B, 2C, and 2D, shows treatment of a large deep pressure ulcer using composition impregnated into acetate non-woven medical grade dressing.

Panels 2A, 2B, 2C, and 2D, depicted in FIG. 2, show treatment using dressings impregnated with composition 1 of the present invention, MGO-fortified buckwheat honey, of a large deep pressure ulcer. The MGO-fortified buckwheat honey dressings were also used to treat a large deep pressure ulcer on the right heel of a 59 year-old male. This patient had a history of diabetes and immobility. Before onset of treatment with the sterile MGO-fortified buckwheat honey dressings, the wound measured approximately 6.3 cm.times.4.4 cm (Panel 2A: 27.7 cm.sup.2). Again the patient was instructed on how to change his own dressings every 48 hours. After three weeks of treatment with the sterile MGO-fortified buckwheat honey dressings, the wound area had decreased to 11.2 cm.sup.2 (Panel 2B), a 60% reduction in the wound area, and again greater than the 50% wound area reduction within 4 weeks of treatment that is indicative of complete closure within a 12-20 week time frame. This large pressure ulcer had reduced in wound area to 4.4 cm.sup.2 after 9 weeks of treatment (Panel 2C), and as expected, went on to completely close after 13 weeks of treatment with the sterile MGO-fortified buckwheat honey wound dressings (Panel 2D).

Example 3 Demonstrates Composition 2, Embodiments 3 and 4

Figure 3:
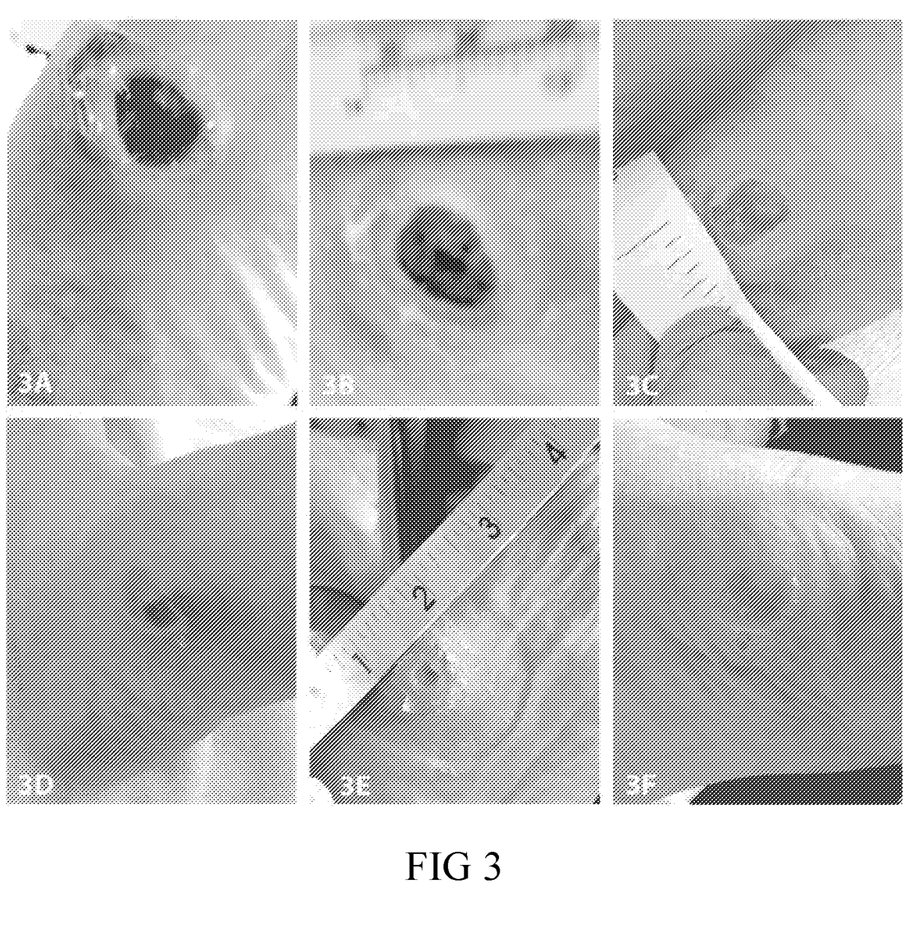
FIG. 3, panels 3A, 3B, 3C, and 3D, 3E, and 3F, shows treatment using composition 2 of the present invention, of a diabetic foot ulcer.

As shown in FIG. 3, Panels 3A, 3B, 3C, 3D, 3E, and 3F, show treatment using dressings impregnated with composition 2 of the present invention, MVE ointment with MGO, of a diabetic foot ulcer. A composition herein referred to as "MVE ointment with MGO" was prepared in two parts as follows: Part A, the PEG phase, was prepared by adding 34.205 g polyethylene glycol (PEG)-400 to a PYREX beaker and heating it to 70.degree. C. While constantly stirring the pre-heated PEG-400, 42.274 g PEG-4000 was added slowly until all the solid PEG-4000 was dissolved into the PEG-400 and the PEG phase was left to cool to 50.degree. C. Part B, the aqueous phase, was prepared by weighing 21.21 g deionized water into a glass beaker and, with constant stirring, dissolving into it 1.681 g magnesium chloride, hexahydrate; 0.387 g potassium chloride; 0.02 g magnesium bromide, hexahydrate; 0.0028 g magnesium sulfate, heptahydrate; 0.0164 g calcium chloride dihydrate; 0.0025 g zinc chloride; 0.0018 g rubidium chloride; and 0.1 g sodium benzoate. The total amount of inorganic minerals, herein referred to as MVE (for multivalent electrolytes), was 2.1115% in weight.

When all the salts had dissolved, the aqueous phase was slowly added to the PEG phase with constant stirring, while the temperature of the PEG phase was initially at 50.degree. C. During the addition of the aqueous phase to the PEG phase, outgassing occurred and the temperature of the solution decreased. The pH of this ointment without adjustment is 4.30 (a 10-fold dilution of a small aliquot of the ointment in water was used to measure the pH). The pH of this ointment can be lowered, if desired by the addition of 50% hydrochloric acid. After the mixture had cooled to 40.degree. C., 0.1 g methylglyoxal was added and the total 100 g of ointment was then transferred to tubes for use. Alternatively, the ointment was impregnated into acetate non-woven medical grade dressing and packaged as per the MGO-fortified buckwheat honey dressings described above.

Figure 4:
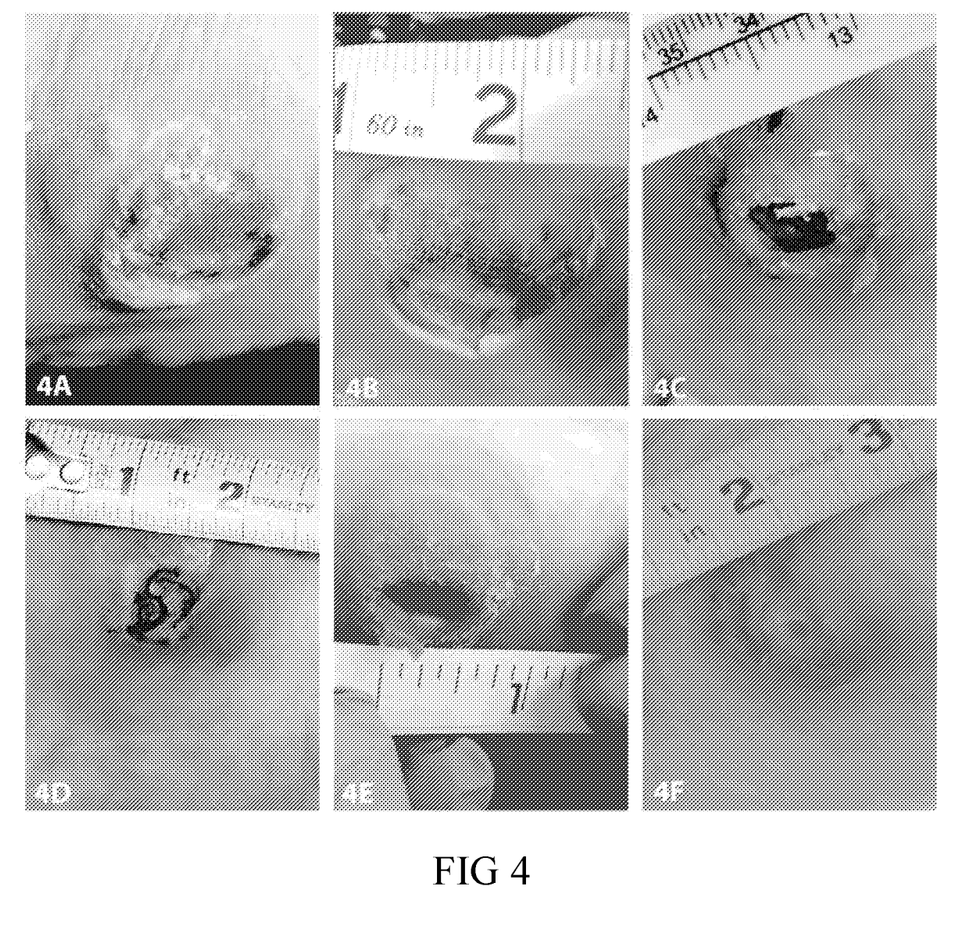
FIG. 4, panels 4A, 4B, 4C, 4D, 4E, and 4F, shows treatment using dressings impregnated with composition 3 of the present invention, of an infected venous leg ulcer.

When applied daily to a diabetic foot ulcer that had become infected and was not healing by previous treatment modalities, the 'MVE ointment with MGO' described herein closed the wound in 19 weeks (see Panels 3A-3F). This wound was on the sole of the left foot of an 82-year-old Caucasian woman with hypertension and a 12-year history of type II diabetes. At age 72 she developed neuropathy and at age 80 she developed a diabetic foot ulcer on the sole of her left foot (Panel 3A), and soon thereafter, a diabetic foot ulcer in about the same position on the sole of her right foot (Panel 4A). Both ulcers had previously been treated unsuccessfully with Regranex for 18 months. Subsequently the left foot ulcer was treated with sterile 'MVE ointment with MGO' applied to sterile gauze and then to the wound. The right foot ulcer (depicted in Panels 4A-4F) was treated with 'buckwheat honey with MVE & MGO' and is described in more detail below]. The 'MVE ointment with MGO' dressings applied to the left foot ulcer were changed every 24 hours (the patient was instructed on how to change her own dressings) and the healing progression is depicted in Panels 3A-3F. Panel 3A represents the wound on the day 'MVE ointment with MGO' treatment started; Panel 3B, after treatment for 2.5 weeks with 'MVE ointment with MGO'; Panel 3C, after treatment for 7.5 weeks with 'MVE ointment with MGO'; Panel 3D, after treatment for 10 weeks with 'MVE ointment with MGO'; Panel 3E, after treatment for 13 weeks with 'MVE ointment with MGO'; Panel 3F, left foot DFU healed after treatment for 19 weeks with 'MVE ointment with MGO.'

Example 4 Demonstrates Composition 3, Embodiment 5

As shown in FIG. 4, Panels 4A, 4B, 4C, 4D, 4E, and 4F, show treatment using dressings impregnated with composition 3 of the present invention, buckwheat honey with MVE & MGO, of a diabetic foot ulcer. A composition, herein referred to as "buckwheat honey with MVE & MGO," was prepared in three parts as follows: Part A, the PEG phase, was prepared by adding 34.205 g polyethylene glycol (PEG)-400 to a PYREX beaker and heating it to 70.degree. C. While constantly stirring the pre-heated PEG-400, 42.274 g PEG-4000 was added slowly until all the solid PEG-4000 was dissolved into the PEG-400 and the PEG phase was left to cool to 50.degree. C.

Part B, 2.times. aqueous phase, was prepared by weighing 21.21 g deionized water into a glass beaker and with constant stirring, dissolving into it 3.362 g magnesium chloride, hexahydrate; 0.774 g potassium chloride; 0.04 g magnesium bromide, hexahydrate; 0.0056 g magnesium sulfate, heptahydrate; 0.0328 g calcium chloride dihydrate; 0.005 g zinc chloride; 0.0036 g rubidium chloride; and 0.1 g sodium benzoate. The total amount of inorganic minerals, herein referred to as MVE (for multivalent electrolytes), was 4.223% in weight. When all the salts had dissolved, the aqueous phase was slowly added to the PEG phase with constant stirring, while the PEG phase was initially at 50.degree. C. During the addition of the aqueous phase to the PEG phase, outgassing occurred and the temperature of the solution decreased. The pH of this ointment without adjustment is 4.30 (a 10-fold dilution of a small aliquot of the ointment in water was used to measure the pH). The pH of this ointment can be lowered, if desired by the addition of 50% hydrochloric acid. After the mixture had cooled to 40.degree. C., 0.1 g methylglyoxal was added.

Part C, one part by volume of the 2.times. MVE ointment with MGO, made as described in Part B, was thoroughly mixed with one part by volume of 'MGO-fortified buckwheat honey,' to make the final 'buckwheat honey with MVE & MGO' product. The ratio of 'MGO-fortified buckwheat honey' (s.g.=1.43 g/mL) to 2.times. 'MVE ointment with MGO' (s.g=1.1 g/mL) can be varied, but as used in the treatment of the diabetic foot ulcer in Panel 4, it was mixed 1:1 (v/v), [or 1.3:1 (w/w)]. The 'buckwheat honey with MVE & MGO' ointment was then transferred to tubes for use. Alternatively the 'buckwheat honey with MVE & MGO' ointment was impregnated into acetate non-woven medical grade dressing and packaged as per the 'MGO-fortified buckwheat honey' dressings described above.

When applied daily to a non-healing infected diabetic foot ulcer, the 'buckwheat honey with MVE & MGO' described herein closed the wound in 17 weeks (see Panels 4A-4F). This wound was on the sole of the right foot of the 82-year-old Caucasian woman described above. Prior to treatment using 'buckwheat honey with MVE & MGO' the wound had been treated with Regranex without noticeable improvement. Sterile 'buckwheat honey with MVE & MGO' was applied to sterile gauze and then to the wound. The dressings were changed daily by the patient who had been instructed on how to change the dressings. The healing progression of this wound is depicted in Panels 4A-4F. Panel 4A represents the wound on the day 'buckwheat honey with MVE & MGO' treatment started; Panel 4B, after treatment for 2.5 weeks with 'buckwheat honey with MVE & MGO'; Panel 4C, after treatment for 5.5 weeks with 'buckwheat honey with MVE & MGO'; Panel 4D, after treatment for 8 weeks with 'buckwheat honey with MVE & MGO'; Panel 4E, after treatment for 12 weeks with 'buckwheat honey with MVE & MGO'; Panel 4F, right foot DFU healed after treatment for 17 weeks with 'buckwheat honey with MVE & MGO.'

Example 5 Demonstrates Composition 2, Embodiments 3 and 4, Variant on Example 3

A composition, herein referred to as "PeloSinus," was prepared by dissolving 1.645 g magnesium chloride, hexahydrate; 0.548 g potassium citrate, monohydrate; 0.019 g magnesium bromide, hexahydrate; 0.0026 g magnesium sulfate, heptahydrate; 0.017 g calcium chloride, dihydrate; 0.0001 g zinc chloride; 0.002 g rubidium chloride; 0.05 g methylglyoxal; and 0.000065 g citric acid in deionized water to a final volume of 100 mL. The total amount of mineral salts, herein referred to as MVE (for multivalent electrolytes), was 2.2337% (w/v). This solution is isotonic with body fluid, having a tonicity of 0.909 g sodium chloride equivalents per 100 mL, and is used for the treatment of internal mucous membranes such as the sinonasal and endometrial linings. It is also used as a wound wash or cleanser. The pH of the solution thus formulated is 6.5. Prior to use the solution is sterilized, for example by filtration or irradiation.

The anti-biofilm activity of this solution was tested in a well-characterized biofilm assay [the assay of which was published by Desrosiers et al., (2007)] and the results are shown in Table 2. Biofilm colonies were grown using two species of bacteria that commonly form biofilm colonies in human wounds, *Pseudomonas aeruginosa* and *Staphylococcus aureus*. As can be seen in Table 2, treatment with 'PeloSinus' solution reduced *Pseudomonas aeruginosa* biofilm colony formation by more than 1 log and it reduced *Staphylococcus aureus* biofilm colony formation by more than 4 logs. Both of these are very significant reductions in the abilities of common wound pathogens to establish in a wound environment. Biofilm is present in about 60% of chronic wounds and is very difficult to eliminate.

TABLE 2

Anti-Biofilm Activity of 'PeloSinus' Formulation Against
*Pseudomonas aeruginosa* and *Staphylococcus aureus* Biofilm Colonies

| | Plate Count | Cells/cm$^2$ | | Plate Count | Cells/cm$^2$ |
|---|---|---|---|---|---|
| Saline Control *Pseudomonas aeruginosa* | | | Saline Control *Staphylococcus aureus* | | |
| Drop 1 | 15 | $8.00 \times 10^8$ | Drop 1 | 5 | $2.67 \times 10^6$ |
| Drop 2 | 26 | $1.39 \times 10^9$ | Drop 2 | 4 | $2.13 \times 10^6$ |
| Drop 3 | 24 | $1.28 \times 10^9$ | Drop 3 | 3 | $1.60 \times 10^6$ |
| Drop 4 | 21 | $1.12 \times 10^9$ | Drop 4 | 4 | $2.13 \times 10^6$ |
| Drop 5 | 29 | $1.55 \times 10^9$ | Drop 5 | 2 | $1.07 \times 10^6$ |
| Average | | $1.23 \times 10^9$ | Average | | $1.92 \times 10^6$ |
| Log | | 9.09 | Log | | 6.28 |
| 'PeloSinus' *Pseudomonas aeruginosa* | | | 'PeloSinus' *Staphylococcus aureus* | | |
| Drop 1 | 12 | $6.40 \times 10^7$ | Drop 1 | 4 | $2.13 \times 10^2$ |
| Drop 2 | 16 | $8.53 \times 10^7$ | Drop 2 | 3 | $1.60 \times 10^2$ |
| Drop 3 | 15 | $8.00 \times 10^7$ | Drop 3 | 2 | $1.07 \times 10^2$ |
| Drop 4 | 14 | $7.47 \times 10^7$ | Drop 4 | 2 | $1.07 \times 10^2$ |
| Drop 5 | 10 | $5.33 \times 10^7$ | Drop 5 | 5 | $2.67 \times 10^2$ |
| Average | | $7.15 \times 10^7$ | Average | | $1.71 \times 10^2$ |
| Log | | 7.85 | Log | | 2.23 |
| Treatment with 'PeloSinus' Anti-Biofilm Results in a 1.24 Log Reduction of *Pseudomonas aeruginosa* Biofilm (9.09-7.85) | | | Treatment with 'PeloSinus' Anti-Biofilm Results in a 4.05 Log Reduction of *Staphylococcus aureus* Biofilm (6.28-2.23) | | |

Irrigation of the sinonasal cavities with sterile isotonic 'PeloSinus' also demonstrated efficacy in an animal model of chronic rhinosinusitis. Relative to the standard of care, normal saline solution, 'PeloSinus' irrigation of the sinuses led to a significantly increased lumen space and faster replenishment of mucociliary cells after surgical mucosal stripping.

Example 6 Demonstrates Composition 2,
Embodiments 3 and 4, Variant of Examples 3 and 5

Two compositions ('PeloWash' and 'PeloFusion') were prepared for the treatment of metritis in thoroughbred, quarter horse and other valuable mares (also for the treatment of metritis in other animals including dogs). These compositions are referred to herein as 'PeloWash' and 'PeloFusion,' which together with 'PeloPurge ('PeloWash'+ DMSO),' constitute a treatment system, herein referred to as 'PeloMetriSystem.' After successful racing and/or performance careers, thoroughbred, quarter horse and other elite performance mares are valuable for breeding. Many such mares, however, either do not get pregnant or can only have one foal, and then contract metritis and can't get pregnant again. Metritis is a disorder characterized by inflammation of the endometrial lining of the uterus and infection with various bacteria, including *Klebsiella, Streptococcus,* and *Pseudomonas* spp. The current standard of care uses irrigation of the endometrial lining of the uterus in mares and dogs with saline (or Lactated Ringer's solution) followed by insertion into the uterus of a solution containing antibiotics. Often systemic antibiotics are given simultaneously. But the continuing problem of bacteria developing resistance to antibiotics continues, and many times antibiotic treatment of metritis is either ineffective or causes undesirable reactions in mares. 'PeloMetriSystem' offers an alternative treatment and consists of three solutions as follows:

Solution 1, a composition herein referred to as 'PeloWash,' is prepared by dissolving 16.872 g magnesium chloride, hexahydrate; 5.628 g potassium citrate, monohydrate; 0.190 g magnesium bromide, hexahydrate; 0.026 g magnesium sulfate, heptahydrate; 0.17 g calcium chloride, dihydrate; 0.001 g zinc chloride; 0.02 g rubidium chloride; and 0.00065 g citric acid in deionized water to a final volume of 1000 mL. This solution is isotonic and has a pH of 6.5.

Solution 2, herein referred to as 'PeloPurge' is constituted by mixing 9 parts (by volume) of Solution 1 ('PeloWash'), with 1 part of 90% dimethylsulfoxide (DMSO) just before use.

Solution 3, a composition herein referred to as 'PeloFusion,' is prepared by dissolving 16.023 g magnesium chloride, hexahydrate; 5.34 g potassium citrate, monohydrate; 0.190 g magnesium bromide, hexahydrate; 0.026 g magnesium sulfate, heptahydrate; 0.17 g calcium chloride, dihydrate; 0.001 g zinc chloride; 0.02 g rubidium chloride; 0.00065 g citric acid; 1 g methylglyoxal; and 30 g polyethylene glycol 4000 in deionized water to a final volume of 1000 mL. This solution is isotonic and has a pH of 6.5.

Four mares were treated with this 'PeloMetriSystem' as follows: First, each mare was tested for the presence of metritis-causing bacteria in their uterus. The endometrial lining of the uterus was washed with two to three liters of 'PeloWash.' This was done by placing 1 L of 'PeloWash' at a time into a mare's uterus and relatively quickly withdrawing the solution again. Whether 2 or 3 L was used was determined by how much debris was present in the eluent of each wash. If testing indicated that metritis-causing bacteria was present in a mare's uterus, that mare was next washed with 1 L 'PeloPurge' solution, which again was relatively quickly withdrawn after application. Finally, 250 mL of 'PeloFusion' solution was placed in a mare's uterus and left there. This solution dissipates naturally—some being absorbed, and some pushed out of the uterus. No systemic antibiotics were used.

Four other 'control' mares were treated with the standard of care as follows: First, each mare was tested for the presence of metritis-causing bacteria in their uterus. The endometrial lining of the uterus was washed with two to three liters of normal saline or isotonic Lactated Ringer's solution, 1 L at a time, each liter being relatively quickly withdrawn after insertion. Whether 2 or 3 L was used was determined by how much debris was present in the eluent of each wash. If testing indicated that metritis-causing bacteria was present in a mare's uterus, that mare was next washed with 1 L of 10% DMSO in normal saline or Lactated Ringer's solution, which again was relatively quickly withdrawn after application. Finally, 250 mL of an antibiotic (Amikacin or Timentin) solution in Tris/EDTA buffer was placed in a mare's uterus and left there. The antibiotic in Tris/EDTA solution was left to dissipate naturally by either absorption or being pushed out of the uterus. Some of the control mares were concurrently treated with systemic antibiotics.

No safety concerns were seen in the group treated with 'PeloMetriSystem,' whereas one of the control mares had an undesirable reaction to the use of systemic antibiotics. In addition, three mares in the 'PeloMetriSystem'-treated group became pregnant after treatment, compared to only two in the control group.

Metritis is a problem in humans as well, where it is most commonly referred to as Pelvic Inflammatory Disease (PID). PID is an infection of the uterus (womb), fallopian tubes, and other reproductive organs that causes symptoms such as lower abdominal pain. It is a serious complication of some sexually transmitted diseases (STDs), especially chlamydia and gonorrhea. PID often damages the fallopian tubes and tissues in and near the uterus and ovaries. PID often leads to serious consequences including infertility, ectopic pregnancy (a pregnancy in the fallopian tube or elsewhere outside of the womb), abscess formation, and chronic pelvic pain.

Prompt and appropriate treatment prevents complications of PID caused by scar tissue forming in response to bacterial damage. This scar tissue blocks or interrupts the normal movement of sperm through the fallopian tubes, or eggs into the uterus, and leads to infertility. Treatment with 'EndoMetriSystem' will also prove to be a useful treatment for PID in humans.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

The invention claimed is:

1. A method of treating a wound, comprising:
providing a wound healing composition consisting essentially of buckwheat honey and methylglyoxal in an amount from about 500 mg to 2000 mg per kg of the total composition; and
contacting the wound with a pharmaceutically-acceptable amount of the wound healing composition effective to promote healing of the wound.

2. The method of claim 1 wherein contacting the wound comprises applying the pharmaceutically-acceptable amount of the wound healing composition to skin.

3. The method of claim 1 further comprising providing a support impregnated with the pharmaceutically-acceptable amount of the wound healing composition, wherein the support is selected from a group consisting of: a fibrous gauze material, a hydrogel, a foam, a film, a hydrocolloid, a collagen, an alginate, and a combination of two or more thereof.

4. The method of claim 1 further comprising adding the wound healing composition to a pharmaceutically-acceptable carrier.

5. The method of claim 4 wherein the pharmaceutically-acceptable carrier is a gel.

6. The method of claim 1 further comprising the step of re-applying the pharmaceutically-acceptable amount of the wound healing composition to the wound daily until the wound is healed.

7. The method of claim 1 further comprising the step of re-applying the pharmaceutically-acceptable amount of the wound healing composition to the wound every two days until the wound is healed.

8. The method of claim 1 further comprising the step of re-applying the pharmaceutically-acceptable amount of the wound healing composition to the wound every three days until the wound is healed.

9. A method of treating a wound, comprising:
providing a carrier dressing support impregnated with a pharmaceutically-acceptable amount of a wound healing composition consisting essentially of buckwheat honey and methylglyoxal in an amount from about 500 mg to 2000 mg per kg of the total composition; and
applying the carrier dressing support to the wound, such that the wound healing composition is substantially in contact with the wound.

10. The method of claim 9 wherein the carrier dressing support includes at least one of a fibrous gauze material, an acetate non-woven medical grade dressing, a hydrogel, a foam, a film, a hydrocolloid, a collagen, and an alginate.

11. The method of claim 9 further comprising a step of applying a new carrier dressing support to the wound daily.

12. The method of claim 9 further comprising a step of applying a new carrier dressing support to the wound every two days.

13. The method of claim 9 further comprising a step of applying a new carrier dressing support to the wound every three days.

14. The method of claim 9 further comprising sterilizing the carrier dressing support prior to use.

* * * * *